(12) United States Patent
Abell et al.

(10) Patent No.: US 10,017,595 B2
(45) Date of Patent: Jul. 10, 2018

(54) METALLIC COMPLEX CATALYST AND POLYMERIZATION METHODS EMPLOYING SAME

(71) Applicant: Bridgestone Corporation, Chuo-ku (JP)

(72) Inventors: Joshua P. Abell, Nashville, TN (US); Zengquan Qin, Copley, OH (US)

(73) Assignee: Bridgestone Corporation, Chuo-ku (JP)

( * ) Notice: Subject to any disclaimer, the term of this patent is extended or adjusted under 35 U.S.C. 154(b) by 0 days.

(21) Appl. No.: 15/315,052

(22) PCT Filed: May 25, 2015

(86) PCT No.: PCT/US2015/032342
§ 371 (c)(1),
(2) Date: Nov. 30, 2016

(87) PCT Pub. No.: WO2015/183770
PCT Pub. Date: Dec. 3, 2015

(65) Prior Publication Data
US 2017/0114171 A1    Apr. 27, 2017

Related U.S. Application Data

(60) Provisional application No. 62/005,917, filed on May 30, 2014.

(51) Int. Cl.
| | | |
|---|---|---|
| C08F 4/52 | (2006.01) | |
| C08F 236/04 | (2006.01) | |
| C08F 236/06 | (2006.01) | |
| C07F 17/00 | (2006.01) | |
| C08F 4/54 | (2006.01) | |

(52) U.S. Cl.
CPC ............ *C08F 236/06* (2013.01); *C07F 17/00* (2013.01); *C08F 4/52* (2013.01); *C08F 4/545* (2013.01); *C08F 236/04* (2013.01); *C08F 2420/04* (2013.01); *C08F 2800/10* (2013.01)

(58) Field of Classification Search
CPC .......... C08F 4/52; C08F 4/545; C08F 236/04; C08F 236/06
See application file for complete search history.

(56) References Cited

U.S. PATENT DOCUMENTS

| | | | |
|---|---|---|---|
| 6,569,799 B1 | 5/2003 | Barbotin et al. | |
| 6,800,705 B2 | 10/2004 | Barbotin et al. | |
| 7,094,854 B2 | 8/2006 | Monteil et al. | |
| 7,300,903 B2 | 11/2007 | Fujita et al. | |
| 7,547,654 B2 | 6/2009 | Boisson et al. | |
| 8,653,290 B2 | 2/2014 | Kaita et al. | |
| 8,853,339 B2 | 10/2014 | Kaita et al. | |
| 8,962,743 B2 | 2/2015 | Kaita et al. | |
| 8,969,496 B2 | 3/2015 | Kaita | |
| 9,056,936 B2 | 6/2015 | Horikawa et al. | |
| 9,074,035 B2 | 7/2015 | Kaita et al. | |
| 9,181,376 B2 | 11/2015 | Horikawa et al. | |
| 9,266,978 B2 | 2/2016 | Kaita et al. | |
| 9,670,302 B2 | 6/2017 | Horikawa et al. | |
| 2017/0114170 A1 | 4/2017 | Qin et al. | |

OTHER PUBLICATIONS

A. Davison et al, "Fluxional Behavior of Substituted Indenyl Derivatives of Silicon and Tin," J. Organometlic Chem., 1970, vol. 23, pp. 407-426 (Elsevier Sequoia S.A.; Netherlands).

D C. Bradley et al., "Three-co-ordination in Lanthanide Chemistry: Tris[bis(trimethylsilyl)amido]lanthanide(III) Compounds," J. Chem. Soc., Chem. Commun.,1972, pp. 349-350 (The Royal Society of Chemistry; London, England).

C.A. Bradley et al., "Synthesis and Characterization of Zirconium and Iron Complexes Containing Substituted Indenyl Ligands: Evaluation of Steric and Electronic Parameters," Organometallics, 2004, vol. 23, pp. 5332-5346 (American Chemical Society; Washington, DC).

J Thuilliez et al., "Alternating Copolymerization of Ethylene and Butadiene with a Neodymocene Catalyst," Angew. Chem. Int. Ed., 2005, vol. 44, pp. 2593-2596 (Wiley-VCH Verlag GmbH & Co.; Weinheim, Germany).

T.J. Woodman et al., "Heterogenized 'Ligand-Free' Lanthanide Catalysts for the Homo- and Copolymerization of Ethylene and 1,3-Butadiene," Macromolecules, 2005, vol. 38, pp. 3060-3067 (American Chemical Society; Washington, DC).

C. Capacchione et al., "Ethylene-Butadiene Copolymerization Promoted by Titanium Complex Containing a Tetradentate [OSSO]-Type Bis(phenolato) Ligand," Macromolecules, 2008, vol. 41, 4573-4575 (American Chemical Society; Washington, DC).

C. Capacchione et al., "Copolymerization of Ethylene with Isoprene Promoted by Titanium Complexes Containing a Tetradentate [OSSO]-Type Bis(phenolato) Ligand," J. Polym. Sci.: A, 2010, vol. 48, pp. 4200-4206 (Wiley Periodicals, Inc.; Hoboken, NJ).

*Primary Examiner* — Caixia Lu
(74) *Attorney, Agent, or Firm* — Meredith E. Hooker; David G. Burleson

(57) ABSTRACT

Metallic complexes having indenyl ligands can be used as an ingredient of a catalyst system. The catalyst system can be used in polymerizations of ethylenically unsaturated hydrocarbon monomers that include both olefins and polyenes. Embodiments of the catalyst system can provide interpolymers that include polyene mer and up to about 40 mole percent ethylene mer. The catalyst system also can be used in solution polymerizations conducted in $C_5$-$C_{12}$ alkanes.

20 Claims, No Drawings

METALLIC COMPLEX CATALYST AND POLYMERIZATION METHODS EMPLOYING SAME

CROSS REFERENCE TO RELATED APPLICATION

This application is a national stage entry of international application no. PCT/US2015/032342, filed 25 May 2015, which claims the benefit of U.S. provisional appl. No. 62/005,917, filed 30 May 2014, the disclosure of which is incorporated herein by reference.

BACKGROUND INFORMATION

Rubber goods such as tire treads often are made from elastomeric compositions that contain one or more reinforcing materials such as, for example, particulate carbon black and silica; see, e.g., *The Vanderbilt Rubber Handbook*, 13th ed. (1990), pp. 603-04.

Good traction and resistance to abrasion are primary considerations for tire treads; however, motor vehicle fuel efficiency concerns argue for a minimization in their rolling resistance, which correlates with a reduction in hysteresis and heat build-up during operation of the tire. Reduced hysteresis and traction are, to a great extent, competing considerations: treads made from compositions designed to provide good road traction usually exhibit increased rolling resistance and vice versa.

Filler(s), polymer(s), and additives typically are chosen so as to provide an acceptable compromise or balance of these properties. Ensuring that reinforcing filler(s) are well dispersed throughout the elastomeric material(s) both enhances processability and acts to improve physical properties. Dispersion of fillers can be improved by increasing their interaction with the elastomer(s), which commonly results in reductions in hysteresis (see above). Examples of efforts of this type include high temperature mixing in the presence of selectively reactive promoters, surface oxidation of compounding materials, surface grafting, and chemically modifying the polymer, typically at a terminus thereof.

Various natural and synthetic elastomeric materials often are used in the manufacture of vulcanizates such as, e.g., tire components. Some of the most commonly employed synthetic materials include high cis polybutadiene, often made by processes employing catalysts, and substantially random styrene/butadiene interpolymers, often made by processes employing free radical or anionic initiators.

Of particular difficulty to synthesize are interpolymers of olefins and polyenes, particularly conjugated dienes, due in large part to the very different reactivities of those two types of ethylenically unsaturated monomers. Their respective susceptibilities to coordinate with the metal atoms of polymerization catalysts differ greatly.

Although difficult to synthesize, such interpolymers are of significant commercial interest. Because polyene and olefin monomers usually originate from different raw materials and are provided via different techniques, manufacturers of elastomeric materials can guard against supply and price disruptions of either monomer by synthesizing interpolymers with varying and/or adjustable amounts of mer from each.

Additionally, certain portions of pneumatic tires, particularly sidewalls, preferably exhibit good resistance to atmospheric degradation, particularly ozone degradation. Such components can benefit from inclusion of substantially saturated elastomer(s). Historically, typical options have included ethylene/propylene/non-conjugated diene (EPDM) interpolymers or brominated copolymers of isobutylene and para-methylstyrene. Alternatives to these materials also remain desirable.

SUMMARY

Any of a class of indenyl-metal complexes can be used as an ingredient of a catalyst system. The catalyst system can be used in polymerizations of ethylenically unsaturated hydrocarbon monomers, including mixtures or blends of polyenes and olefins.

The class of metallic complexes can be represented by the general formula

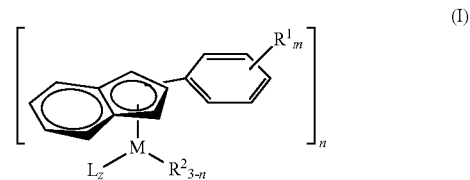

where
M represents a Group 3 metal atom;
L represents a neutral Lewis base;
z is an integer of from 0 to 3 inclusive;
m is an integer of from 1 to 5 inclusive;
n is 1 or 2;
each $R^1$ is an electron withdrawing (R') or electron rich (R") group or atom; and
$R^2$ is an X-type, monoanionic ligand.
The $R^1$-substituted phenyl group is attached at either the 2 or 3 position of the indenyl ligand.

In formula (I), an L group and an $R^2$ group optionally can join so as to provide, together with the M atom to which each is bonded, a cyclic moiety.

In other aspects are provided a catalyst composition that includes the formula (I) complex with a catalyst activator. Methods of making the complex of formula (I) and the catalyst composition also are provided.

In a still further aspect is provided a process of polymerizing ethylenically unsaturated hydrocarbon monomers. The method involves contacting the monomers with the aforedescribed catalyst composition. The ethylenically unsaturated hydrocarbon monomers advantageously can include one or more types of polyene and, optionally, one or more types of olefin.

In certain embodiments, the polymerization process can result in low amounts of vinyl polyene mer, i.e., the polyene mer preferentially incorporates in a 1,4-configuration.

The foregoing polymerization processes also optionally can include providing the resulting polymer with a terminal moiety that includes one or more heteroatoms so as to enhance the ability of the polymer to interact with a variety of types of particulate filler such as, e.g., carbon black and/or silica.

Also provided are compositions, including vulcanizates, that include particulate fillers and the resulting polymers, certain embodiments of which may also include terminal functionality, as are methods of providing and using such compositions.

Other aspects of the invention will be apparent to the ordinarily skilled artisan from the detailed description that follows. To assist in understanding that description, certain definitions are provided immediately below, and these are intended to apply throughout unless the surrounding text explicitly indicates a contrary intention:

"polymer" means the polymerization product of one or more monomers and is inclusive of homo-, co-, ter-, tetra-polymers, etc.;

"mer" and "mer unit" both mean that portion of a polymer derived from a single reactant molecule (e.g., ethylene mer has the general formula —$CH_2CH_2$—);

"copolymer" means a polymer that includes mer units derived from two reactants, typically monomers, and is inclusive of random, block, segmented, graft, etc., copolymers;

"interpolymer" means a polymer that includes mer units derived from at least two reactants, typically monomers, and is inclusive of copolymers, terpolymers, tetra-polymers, and the like;

"substituted" means containing a heteroatom or functionality (e.g., hydrocarbyl group) that does not interfere with the intended purpose of the group in question;

"polyene" means a molecule, typically a monomer, with at least two double bonds located in the longest portion or chain thereof, and specifically is inclusive of dienes, trienes, and the like;

"polydiene" means a polymer that includes mer units from one or more dienes;

"lanthanide metal" means any element having an atomic number of 57-71 inclusive;

"Group 3 metal" means Sc, Y or a lanthanide metal;

"phr" means parts by weight (pbw) per 100 pbw rubber;

"radical" means the portion of a molecule that remains after reacting with another molecule, regardless of whether any atoms are gained or lost as a result of the reaction;

"neutral Lewis base" means a non-ionic compound (or radical) that includes an available pair of electrons;

"aryl" means a phenyl or polycyclic aromatic radical;

"aralkyl" means an alkyl radical that includes an aryl substituent, e.g., a benzyl group;

"non-coordinating anion" means a sterically bulky anion that does not form coordinate bonds with, for example, the active center of a catalyst system due to steric hindrance;

"non-coordinating anion precursor" means a compound that is able to form a non-coordinating anion under reaction conditions;

"terminus" means an end of a polymeric chain;

"terminally active" means a polymer with a living or pseudo-living terminus; and "terminal moiety" means a group or functionality located at a terminus.

Throughout this document, all values given in the form of percentages are weight percentages unless the surrounding text explicitly indicates a contrary intention. The relevant portion(s) of any specifically referenced patent and/or published patent application are incorporated herein by reference.

DETAILED DESCRIPTION OF ILLUSTRATIVE EMBODIMENTS

As apparent from the foregoing, the catalyst composition can be used to polymerize one or more types of polyene, optionally but in some respects preferably in combination with one or more types of olefins.

The resulting polymer can be elastomeric, including mer units that themselves include ethylenic unsaturation. Mer units that include ethylenic unsaturation can be derived from polyenes, particularly dienes and trienes (e.g., myrcene). Illustrative polyenes include $C_4$-$C_{30}$ dienes, preferably $C_4$-$C_{12}$ dienes. Preferred among these are conjugated dienes such as, but not limited to, 1,3-butadiene, 1,3-pentadiene, 1,3-hexadiene, 1,3-octadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, 2,4-hexadiene, and the like.

A polymer that has an overall 1,2-microstructure of no more than 50%, preferably no more than ~35%, based on total polyene content is considered to be "substantially linear." For certain end use applications, however, keeping the content of 1,2-linkages even lower—e.g., to less than 20%, less than 15%, less than 10%, less than 7%, less than 5%, less than 2%, or less than 1% —can be desirable.

Those polyene mer not incorporating into a polymer chain in a 1,2-microstructure can have either a cis or trans isomeric configuration. Polymers that have high cis-1,4-linkage contents, which are desirable for certain end use applications, can be difficult or inefficient to achieve via free radical or anionic (living) polymerizations and, therefore, commonly are prepared by processes using catalysts, as opposed to the initiators employed in living polymerizations.

The present process can provide polymers with polydiene mer having a cis-1,4-linkage content of at least ~60%, at least ~75%, at least ~85%, at least ~90%, and even at least ~95%, with each of the foregoing representing a numerical percentage relative to total polyene content.

Examples of olefins that can be employed in the polymerization process include $C_2$-$C_{30}$, preferably $C_2$-$C_{20}$ and more preferably $C_2$-$C_{12}$, straight chain or branched α-olefins such as ethylene, propylene, 1-butene, 1-pentene, 3-methyl-1-butene, 1-hexene, 4-methyl-1-pentene, 3-methyl-1-pentene, 1-octene, 1-decene, 1-dodecene, 1-tetradecene, 1-hexadecene, 1-octadecene, 1-eicosene, and the like, as well as $C_3$-$C_{30}$ cycloolefins such as cyclopentene, cycloheptene, norbornene, 5-methyl-2-norbornene, and tetracyclododecene.

The polymerization process can provide an olefin/polyene interpolymer, typically one with a predominant amount of polyene mer, e.g., an olefin/conjugated diene copolymer that includes more conjugated diene mer than olefin mer. The resulting interpolymer can contain up to 10, 20, 30, 40 or even perhaps 45% olefin mer and often at least 60, 70, 80 or even 90% polyene mer. In terms of ranges, the interpolymer can include from 1 to 45% olefin mer and from 55 to 99% conjugated diene mer, from ~3 to 40% olefin mer and from 60 to 97% conjugated diene mer, from 5 to 35% olefin mer and from 65 to 95% conjugated diene mer, or from ~7 to 30% olefin mer and from 70 to 93% conjugated diene mer. (All percentages in this paragraph are mole percents.)

The number average molecular weight ($M_n$) of a polymer produced according to the disclosed methods typically is such that a quenched sample exhibits a gum Mooney viscosity ($ML_{1+4}$/100° C.) of from ~2 to ~150, more commonly from ~2.5 to ~125, even more commonly from ~5 to ~100, and most commonly from ~10 to ~75; the foregoing generally corresponds to a $M_n$ of from ~5,000 to ~250,000 Daltons, commonly from ~10,000 to ~150,000 Daltons, more commonly from ~50,000 to ~120,000 Daltons, and most commonly from ~10,000 to ~100,000 Daltons or even ~10,000 to ~80,000 Daltons. The resulting interpolymer typically has a molecular weight distribution ($M_w/M_n$) of from 1 to 20, commonly from 2 to 15, and more commonly from 3 to 10. (Both $M_n$ and $M_w$ can be determined by GPC using polystyrene standards for calibration.)

The foregoing types of polymers can be made by solution polymerization, which affords exceptional control of properties as randomness, microstructure, etc. Solution polymerizations have been performed since about the mid-20th century, so the general aspects thereof are known to the ordinarily skilled artisan; nevertheless, certain aspects are provided here for convenience of reference.

Suitable solvents include those organic compounds that do not undergo polymerization or incorporation into propagating polymer chains (i.e., are inert toward and unaffected by the catalyst composition) and preferably are liquid at ambient temperature and pressure. Examples of suitable organic solvents include hydrocarbons with relatively low boiling points such as aromatic hydrocarbons and (cyclo) aliphatic hydrocarbons. Exemplary polymerization solvents include various $C_5$-$C_{12}$ cyclic and acyclic alkanes (e.g., n-pentane, n-hexane, n-heptane, n-octane, n-nonane, n-decane, isopentane, isohexanes, isooctanes, 2,2-dimethylbutane, cyclopentane, cyclohexane, methylcyclopentane, methylcyclohexane, etc.) as well as their alkylated derivatives, certain liquid aromatic compounds (e.g., benzene, toluene, xylenes, ethylbenzene, diethylbenzene, and mesitylene), petroleum ether, kerosene, petroleum spirits, and mixtures thereof. Other potentially suitable organic compounds that can be used as solvents include high-boiling hydrocarbons of high molecular weights such as paraffinic oil, aromatic oil, or other hydrocarbon oils that are commonly used to oil-extend polymers. The ordinarily skilled artisan is aware of other useful solvent options and combinations.

In the polymerization process, a catalyst composition that includes a Group 3 metal complex is employed. The term "catalyst composition" encompasses a simple mixture of ingredients, a complex of various ingredients that results from physical or chemical forces of attraction, a chemical reaction product of some or all of the ingredients, or a combination of the foregoing.

Exemplary catalyst compositions include (a) a formula (I) complex, an alkylating agent and optionally a halogen-containing compound (where neither the formula (I) complex or the alkylating agent contains a halogen atom); (b) a formula (I) complex and an aluminoxane; or (c) a formula (I) complex, an alkylating agent, and a non-coordinating anion or precursor thereof. Each component of these exemplary compositions is discussed separately below.

The polymerization processes employ a specific genus of Group 3 metal complexes, specifically, those defined by formula (I) set forth above. The complex can be formed prior to introduction to the polymerization vessel, or components (reactants) can be added separately and permitted to react so as to form the complex (catalyst) in situ.

In formula (I), M represents a Group 3 metal atom. Where M is a lanthanide series metal, it preferably is Nd or Gd. M can be in any of a number of oxidation states, with +2 to +5 being common and +3 being perhaps the most common.

Again referring to formula (I), L represents a neutral Lewis base, examples of which include but are not limited to cyclic or acyclic (thio)ethers, amines, and phosphines. Specific non-limiting examples of L groups include THF, diethyl ether, dimethyl aniline, trimethyl phosphine, neutral olefins, neutral diolefins, and the like. Use of ethers and cyclic ethers as L in formula (I) complexes can be preferred.

Again referring to formula (I), z can be an integer of from 0 to 3 (determined by the available coordination number(s) of M), so the complex can contain no L groups, one L group, or a plurality of L groups. In some embodiments, preference can be given to complexes where z is 0; examples of such embodiments are given below in the examples section. Where z is 2 or 3, each L can be the same or different, although preference can be given to those complexes where each L is the same.

Again referring to formula (I), each $R^2$ independently is an X-type, monoanionic ligand (of the CBC method, see Green, M. L. H. "A new approach to the formal classification of covalent compounds of the elements," *J. Organomet. Chem.*, 500 (1-2), pp. 127-48 (1995)). Non-limiting examples of $R^2$ include H; a halogen atom, especially Cl or Br; a silyl group; a siloxy group; a nitro group; a sulfonate group; an amido group; a silylalkyl group; an alkoxy, particularly a $C_1$-$C_6$ alkoxy, group; and a $C_1$-$C_{20}$, particularly a $C_1$-$C_{12}$, substituted or unsubstituted, straight-chain or branched (perfluoro)alkyl group (including, but not limited to, methyl, ethyl, n-propyl, isopropyl, n-butyl, isobutyl, sec-butyl, tert-butyl, neopentyl, n-hexyl, and octyl), aralkyl group, allyl group, amino group or substituted or unsubstituted aryl group (including, but not limited to, phenyl, tolyl, benzyl, naphthyl, biphenyl, phenanthryl, anthracenyl and terphenyl). Al- and B-containing groups represented, respectively, by $AlR^7_4$ and $BR^7_4$ where $R^7$ is H, a halogen atom, a substituted or unsubstituted aryl group, etc., also can serve as an $R^2$ group. Those embodiments where $R^2$ bonds to or associates with M via a C atom might permit the use of simpler catalysts systems, a point discussed in more detail below. Any of a variety of bis(silyl) amino groups constitute preferred $R^2$ groups in certain embodiments.

For substituted $R^2$ groups, exemplary substituents include, but are not limited to halogen atoms, halo-substituted groups (e.g., halogenated $C_1$-$C_{30}$, particularly $C_1$-$C_8$, hydrocarbyl groups such as trifluoromethyl, pentafluorophenyl, and chlorophenyl), other $C_1$-$C_{30}$, particularly $C_1$-$C_8$, hydrocarbyl groups (e.g., aryl-substituted alkyl groups such as benzyl and cumyl), heteroatom-containing groups (e.g., alkoxy, aryloxy such as 2,6-dimethylphenoxy or 2,4,6-trimethylphenoxy, acyl such as p-chlorobenzoyl or p-methoxybenzoyl, (thio)carboxyl, carbonato, hydroxy, peroxy, (thio) ester such as acetyloxy or benzoyloxy, (thio)ether, anhydride, amino, imino, amide such as acetamido or N-methylacetamido, imide such as acetimido and benzimido, hydrazino, hydrazono, nitro, nitroso, cyano, isocyano, (thio)cyanic acid ester, amidino, diazo, borandiyl, borantriyl, diboranyl, mercapto, dithioester, alkylthio, arylthio such as (methyl)phenylthio, or naphthylthio, thioacyl, isothiocyanic acid ester, sulfonester, sulfonamide, dithiocarboxyl, sulfo, sulfonyl, sulfinyl, sulfenyl, sulfonate, phosphido, (thio)phosphoryl, phosphato, silyl, siloxy, hydrocarbyl-substituted silyl groups such as methylsilyl, dimethylsilyl, trimethylsilyl, ethylsilyl, diethylsilyl, triethylsilyl, diphenylmethylsilyl, triphenylsilyl, dimethylphenylsilyl, dimethyl-t-butylsilyl, dimethyl(pentafluorophenyl)silyl, bistrimethylsilylmethyl, and hydrocarbyl-substituted siloxy groups such as trimethylsiloxy), and the like. (Replacing the silicon atom in the Si-containing groups with Ge or Sn can provide useful Ge- or Sn-containing groups.)

Alternatively, one $R^2$ and one L, together with the M atom, can join to form a cyclic moiety, typically a 5- or 6-membered ring that optionally contains one or more heteroatoms in addition to the M atom. Optionally, the cyclic moiety can include one or more pendent substituents such as, but not limited to, substituted or unsubstituted $C_1$-$C_{20}$ (particularly $C_1$-$C_6$) alkyl groups.

Again referring to formula (I), each $R^1$ is an atom or functional group that is electron withdrawing (R') or electron rich (R"), i.e., able to draw electrons toward itself or push electrons toward the phenyl ring, respectively. For descriptions of electron withdrawing and electron rich groups, the interested reader is directed to any of a variety of texts such as F. Carey, *Organic Chemistry*, 6th ed., McGraw-Hill College (2006; New York, N.Y.). Non-limiting examples of R' atoms and groups include halogens, haloalkyl (including perfluoroalkyl) groups, nitro groups, nitrile groups, sulfonate groups and the like. Non-limiting examples of R" groups include $C_1$-$C_{12}$, typically $C_1$-$C_6$ and preferably $C_1$-$C_4$ substituted and unsubstituted alkyl groups, cycloalkyl groups, alkoxy groups (and sulfur analogs), amido groups and the like.

The variable m in formula (I)-type complexes is an integer of from 1 to 5, inclusive. Where m≥2, each $R^1$ preferably is either R' or R", i.e., the presence of both R' and R" groups on the same phenyl ring is not preferred, although each $R^1$ need not be identical. If an $R^1$ group is relatively bulky, m might be limited to being 3 or less. Where $R^1$ is R", two or more R" groups can join so as to provide a substituted or unsubstituted hydrocarbylene group which, with two phenyl ring C atoms, provides a non-aromatic carbocyclic moiety.

Again referring to formula (I), the variable n can be either 1 or 2, with the resulting complexes being represented below by, respectively, formulas (Ia) and (Ib):

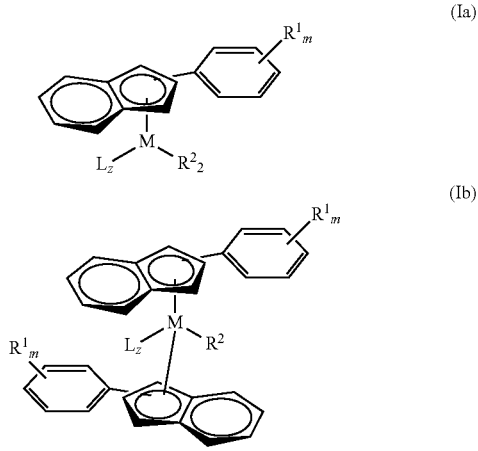

Depending on the value of z, M in the formula (Ia) complexes can be bonded to from 3 to 6 other atoms. The coordination numbers of Group 3 metal atoms, particularly lanthanide metal atoms, in organometallic complexes can range from 3 to 12, with the bulkiness of the ligands being the primary deciding factor on the upper limit. Such metal atoms typically have a coordination number of at least 6, but bulky ligands can result in lower coordination numbers. Therefore, particularly where $R^2$ is a relatively bulky ligand, z might be limited to 0 to 2 inclusive, or even 0 or 1.

Again referring to formula (I), the substituted phenyl moiety (or moieties, in the case of n=2) can be attached at either the 2- or 3-positions of the indenyl group(s). Using the formula (Ia) complex above for exemplary purposes, the 2- and 3-substituted species are represented below by, respectively, formulas (Ia-1) and (Ia-2):

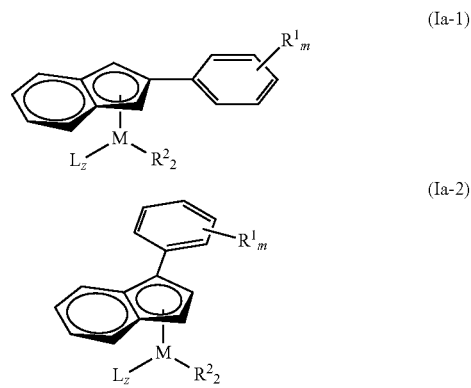

(The ordinarily skilled artisan can easily extend this description to envision the substitutions on the general formula (Ib)-type bis complexes.)

Formula (I)-type complexes can be prepared following a procedure similar to that described in the examples section below, the teaching of which can be extended or modified readily by the ordinarily skilled artisan.

Component (b) of the catalyst composition, referred to herein as a co-catalyst or catalyst activator, includes an alkylating agent and/or a compound containing a non-coordinating anion or a non-coordinating anion precursor.

An alkylating agent can be considered to be an organometallic compound that can transfer hydrocarbyl groups to another metal. These agents typically are organometallic compounds of electropositive metals such as Groups 1, 2, and 3 metals. Exemplary alkylating agents include organoaluminum compounds such as those having the general formula $AlR^8_oX_{3-o}$ where o is an integer of from 1 to 3 inclusive; each $R^8$ independently is a monovalent organic group, which may contain heteroatoms such as N, O, B, Si, S, P, and the like, connected to the Al atom via a C atom; and each X independently is H, a halogen atom, a carboxylate group, an alkoxide group, or an aryloxide group. In one or more embodiments, each $R^8$ independently can be a hydrocarbyl group such as, for example, alkyl, cycloalkyl, substituted cycloalkyl, alkenyl, cycloalkenyl, substituted cycloalkenyl, aryl, substituted aryl, aralkyl, alkaryl, allyl, and alkynyl groups, with each group containing from a single C atom, or the appropriate minimum number of C atoms to form the group, up to about 20 C atoms. These hydrocarbyl groups may contain heteroatoms including, but not limited to, N, O, B, Si, S, and P atoms. Non-limiting species of organoaluminum compounds within this general formula include trihydrocarbylaluminum compounds such as trimethylaluminum, triethylaluminum, triisobutylaluminum (TIBA), tri-n-propylaluminum, triisopropylaluminum, tri-n-butylaluminum, tri-t-butylaluminum, tri-n-pentylaluminum, trineopentylaluminum, tri-n-hexylaluminum, tri-n-octylaluminum, tris(2-ethylhexyl)aluminum, tricyclohexylaluminum, tris(1-methylcyclopentyl)aluminum, triphenylaluminum, tri-p-tolylaluminum, tris(2,6-dimethylphenyl)aluminum, tribenzylaluminum, diethylphenylaluminum, diethyl-p-tolylaluminum, diethylbenzylaluminum, ethyldiphenylaluminum, ethyldi-p-tolylaluminum, and ethyldibenzylaluminum;

dihydrocarbylaluminum hydrides such as diethylaluminum hydride, di-n-propylaluminum hydride, diisopropylaluminum hydride, di-n-butylaluminum hydride, diisobutylaluminum hydride (DIBAH), di-n-octylaluminum hydride, diphenylaluminum hydride, di-p-tolylaluminum hydride, dibenzylaluminum hydride, phenylethylaluminum hydride, phenyl-n-propylaluminum hydride, phenylisopropylaluminum hydride, phenyl-n-butylaluminum hydride, phenylisobutylaluminum hydride, phenyl-n-octylaluminum hydride, p-tolylethylaluminum hydride, p-tolyl-n-propylaluminum hydride, p-tolylisopropylaluminum hydride, p-tolyl-n-butylaluminum hydride, p-tolylisobutylaluminum hydride, p-tolyl-n-octylaluminum hydride, benzylethylaluminum hydride, benzyl-n-propylaluminum hydride, benzylisopropylaluminum hydride, benzyl-n-butylaluminum hydride, benzylisobutylaluminum hydride, and benzyl-n-octylaluminum hydride;

hydrocarbylaluminum dihydrides such as ethylaluminum dihydride, n-propylaluminum dihydride, isopropylaluminum dihydride, nbutylaluminum dihydride, isobutylaluminum dihydride, and n-octylaluminum dihydride;

dihydrocarbylaluminum carboxylates;

hydrocarbylaluminum bis(carboxylate)s;

dihydrocarbylaluminum alkoxides;

hydrocarbylaluminum dialkoxides;

dihydrocarbylaluminum halides such as diethylaluminum chloride (DEAC), di-n-propylaluminum chloride, diisopropylaluminum chloride, di-n-butylaluminum chloride, diisobutylaluminum chloride, di-n-octylaluminum chloride, diphenylaluminum chloride, di-p-tolylaluminum chloride, dibenzylaluminum chloride, phenylethylaluminum chloride, phenyl-n-propylaluminum chloride, phenylisopropylaluminum chloride, phenyl-n-butylaluminum chloride, phenylisobutylaluminum chloride, phenyl-n-octylaluminum chloride, ptolylethylaluminum chloride, p-tolyl-n-propylaluminum chloride, p-tolylisopropylaluminum chloride, p-tolyl-n-butylaluminum chloride, p-tolylisobutylaluminum chloride, p-tolyl-noctylaluminum chloride, benzylethylaluminum chloride, benzyl-n-propylaluminum chloride, benzylisopropylaluminum chloride, benzyl-n-butylaluminum chloride, benzylisobutylaluminum chloride, and benzyl-n-octylaluminum chloride;

hydrocarbylaluminum dihalides such as ethylaluminum dichloride, n-propylaluminum dichloride, isopropylaluminum dichloride, n-butylaluminum dichloride, isobutylaluminum dichloride, and n-octylaluminum dichloride;

dihydrocarbylaluminum aryloxides; and hydrocarbylaluminum diaryloxides.

In certain embodiments, the alkylating agent can include trihydrocarbylaluminum, dihydrocarbylaluminum hydride, and/or hydrocarbylaluminum dihydride.

Other organoaluminum compounds that can serve as alkylating agents include, but are not limited to, dimethylaluminum hexanoate, diethylaluminum octoate, diisobutylaluminum 2-ethylhexanoate, dimethylaluminum neodecanoate, diethylaluminum stearate, diisobutylaluminum oleate, methylaluminum bis(hexanoate), ethylaluminum bis(octoate), isobutylaluminum bis(2-ethylhexanoate), methylaluminum bis(neodecanoate), ethylaluminum bis(stearate), isobutylaluminum bis(oleate), dimethylaluminum methoxide, diethylaluminum methoxide, diisobutylaluminum methoxide, dimethylaluminum ethoxide, diethylaluminum ethoxide, diisobutylaluminum ethoxide, dimethylaluminum phenoxide, diethylaluminum phenoxide, diisobutylaluminum phenoxide, methylaluminum dimethoxide, ethylaluminum dimethoxide, isobutylaluminum dimethoxide, methylaluminum diethoxide, ethylaluminum diethoxide, isobutylaluminum diethoxide, methylaluminum diphenoxide, ethylaluminum diphenoxide, and isobutylaluminum diphenoxide.

Aluminoxanes constitute another class of organoaluminum compounds suitable for use as an alkylating agent. (These compounds also can serve as activators after the alkylating activity is complete.) This class includes oligomeric linear aluminoxanes and oligomeric cyclic aluminoxanes, formulas for both being provided in a variety of references including, for example, U.S. Pat. No. 8,017,695. (Where the oligomeric type of compound is used as an alkylating agent, the number of moles refers to the number of moles of Al atoms rather than the number of moles of oligomeric molecules, a convention commonly employed in the art of catalyst systems utilizing aluminoxanes.)

Aluminoxanes can be prepared by reacting trihydrocarbylaluminum compounds with water. This reaction can be performed according to known methods such as, for example, (1) dissolving the trihydrocarbylaluminum compound in an organic solvent and then contacting it with water, (2) reacting the trihydrocarbylaluminum compound with water of crystallization contained in, for example, metal salts, or water adsorbed in inorganic or organic compounds, or (3) reacting the trihydrocarbylaluminum compound with water in the presence of the monomer(s) to be polymerized.

Suitable aluminoxane compounds include, but are not limited to, methylaluminoxane (MAO), modified methylaluminoxane (MMAO, formed by substituting ~20 to 80% of the methyl groups of MAO with $C_2$-$C_{12}$ hydrocarbyl groups, preferably with isobutyl groups, using known techniques), ethylaluminoxane, n-propylaluminoxane, isopropylaluminoxane, butylaluminoxane, isobutylaluminoxane, n-pentylaluminoxane, neopentylaluminoxane, n-hexylaluminoxane, n-octylaluminoxane, 2-ethylhexylaluminoxane, cyclohexylaluminoxane, 1-methylcyclopentylaluminoxane, phenylaluminoxane, and 2,6-dimethylphenylaluminoxane.

Aluminoxanes can be used alone or in combination with other organoaluminum compounds. In one embodiment, MAO and at least one other organoaluminum compound such as DIBAH can be employed in combination. The interested reader is directed to U.S. Pat. No. 8,017,695 for other examples of aluminoxanes and organoaluminum compounds employed in combination.

Also suitable as alkylating agents are organozinc (particularly dialkyl zinc) compounds as well as organomagnesium compounds such as those having the general formula $R^9{}_g MgX_{2-g}$ where X is defined as above, g is 1 or 2, and $R^9$ is the same as $R^8$ except that each monovalent organic group is connected to the Mg atom via a C atom. Potentially useful organomagnesium compounds include, but are not limited to, diethylmagnesium, di-npropylmagnesium, diisopropylmagnesium, dibutylmagnesium, dihexylmagnesium, diphenylmagnesium, dibenzylmagnesium, hydrocarbylmagnesium hydride (e.g., methylmagnesium hydride, ethylmagnesium hydride, butylmagnesium hydride, hexylmagnesium hydride, phenylmagnesium hydride, and benzylmagnesium hydride), hydrocarbylmagnesium halide (e.g., methylmagnesium chloride, ethylmagnesium chloride, butylmagnesium chloride, hexylmagnesium chloride, phenylmagnesium chloride, benzylmagnesium chloride, methylmagnesium bromide, ethylmagnesium bromide, butylmagnesium bromide, hexylmagnesium bromide, phenylmagnesium bromide, and benzylmagnesium bromide), hydrocarbylmagnesium carboxylate (e.g., methylmagnesium hexanoate, ethylmagnesium hexanoate, butylmagnesium hexanoate, hexylmagnesium hexanoate, phenylmagnesium hexanoate, and benzylmagnesium hexanoate), hydrocarbylmagnesium alkoxide (e.g., methylmagnesium ethoxide, ethylmagnesium ethoxide, butylmagnesium ethoxide, hexylmagnesium ethoxide, phenylmagnesium ethoxide, and benzylmagnesium ethoxide), and hydrocarbylmagnesium aryloxide (e.g., methylmagnesium phenoxide, ethylmagnesium phenoxide, butylmagnesium phenoxide, hexylmagnesium phenoxide, phenylmagnesium phenoxide, and benzylmagnesium phenoxide).

The catalyst composition also or alternatively can contain a non-coordinating anion or a non-coordinating anion precursor. Exemplary non-coordinating anions include borate anions, particularly fluorinated tetraarylborate anions. Specific examples of non-coordinating anions include tetraphenylborate, tetrakis(monofluorophenyl) borate, tetrakis(difluorophenyl) borate, tetrakis(trifluororphenyl) borate, tetrakis(tetrafluorophenyl) borate, tetrakis(pentafluorophenyl) borate, tetrakis(tetrafluoromethylphenyl) borate, tetra(tolyl) borate, tetra(xylyl) borate, [tris(phenyl), pentafluorophenyl] borate, [tris(pentafluorophenyl), phenyl] borate, tridecahydride-7,8-dicarbaundecaborate and the like. Tetrakis(pentafluorophenyl) borate is among the preferred non-coordinating anions.

Compounds containing a non-coordinating anion also contain a countercation such as a carbonium (e.g., trisubstituted carbonium cation such as triphenylcarbonium cation, tri(substituted phenyl)carbonium cation (e.g., tri(methylphenyl)carbonium cation), oxonium, ammonium (e.g., trialkyl ammonium cations, N,N-dialkyl anilinium cations, dialkyl ammonium cations, etc.), phosphonium (e.g., triaryl phosphonium cations such as triphenyl phosphonium cation, tri(methylphenyl)phosphonium cation, tri(dimethylphenyl) phosphonium cation, etc.), cycloheptatrieneyl, or ferrocenium cation (or similar). Among these, N,N-dialkyl anilinium or carbonium cations are preferred, with the former being particularly preferred.

Examples of compounds containing a non-coordinating anion and a counter cation include triphenylcarbonium tetrakis(pentafluorophenyl)borate, N,N-dimethylanilinium tetrakis(pentafluorophenyl)borate, triphenylcarbonium tetrakis [3,5-bis(trifluoromethyl)phenyl]borate, and N,N-dimethylanilinium tetrakis[3,5-bis(trifluoromethyl)phenyl] borate.

Exemplary non-coordinating anion precursors include boron compounds that include strong electron-withdrawing groups. Specific examples include triarylboron compounds where each aryl group is strongly electron withdrawing, e.g., pentafluorophenyl or 3,5-bis(trifluoromethyl)phenyl.

Catalyst compositions of the type just described have very high catalytic activity for polymerizing polyenes such as conjugated dienes (and optionally olefins, particularly α-olefins) into stereospecific polymers over a wide range of concentrations and ratios, although polymers having the most desirable properties typically are obtained from systems that employ a relatively narrow range of concentrations and ratios of ingredients. Further, the catalyst composition ingredients are believed to interact to form an active catalyst species, so the optimum concentration for each ingredient can depend on the concentrations of the other ingredients. The following molar ratios are considered to be relatively exemplary for a variety of different systems based on the foregoing ingredients:

alkylating agent to formula (I) complex: from ~1:1 to ~1000:1, commonly from ~2:1 to ~500:1, typically from ~5:1 to ~200:1;

aluminoxane to formula (I) complex, specifically equivalents of aluminum atoms in the aluminoxane to equivalents of Group 3 atoms in the complex: from ~5:1 to ~1000:1, commonly from ~10:1 to ~700:1, typically from ~20:1 to ~500:1;

organoaluminum compound to formula (I) complex: from ~1:1 to ~200:1, commonly from ~2:1 to ~150:1, typically from ~5:1 to ~100:1; and non-coordinating anion or precursor to formula (I) complex: from ~1:2 to ~20:1, commonly from ~3:4 to ~10:1, typically from ~1:1 to ~6:1.

The molecular weight of polymers produced with a formula (I) complex-containing catalyst composition can be controlled by adjusting the amount of metallic complex used and/or the amounts of co-catalyst compound concentrations within the catalyst composition; polymers having a wide range of molecular weights can be produced in this manner. In general, increasing the metallic complex and co-catalyst concentrations reduces the molecular weight of resulting polymers, although very low molecular weight polymers (e.g., liquid polydienes) require extremely high catalyst concentrations. Typically, this necessitates removal of catalyst residues from the polymer to avoid adverse effects such as retardation of the sulfur cure rate.

A formula (I) complex-containing catalyst composition can be formed using any of the following methods:

(1) In situ. The catalyst ingredients are added to a solution containing monomer and solvent (or simply bulk monomer). The addition can occur in a stepwise or simultaneous manner. In the case of the latter, the alkylating agent preferably is added first followed by the formula (I) complex.

(2) Pre-mixed. The ingredients can be mixed outside the polymerization system, generally at a temperature of from about −20° to ~80° C., before being introduced to the monomer(s).

(3) Pre-formed in the presence of monomer(s). The catalyst ingredients are mixed in the presence of a small amount of monomer(s) at a temperature of from about −20° to ~80° C. The amount of monomer(s) can range from ~1 to ~500 moles, commonly from ~5 to ~250 moles, typically from ~10 to ~100 moles, per mole of the formula (I) complex. The resulting catalyst composition is added to the remainder of the monomer(s) to be polymerized.

(4) Two-stage procedure.
 (a) The alkylating agent is combined with the formula (I) complex in the absence of monomer or in the presence of a small amount of monomer(s) at a temperature of from about −20° to ~80° C.
 (b) The foregoing mixture and the remaining components are charged in either a stepwise or simultaneous manner to the remainder of the monomer(s) to be polymerized.

When a solution of one or more of the catalyst ingredients is prepared outside the polymerization system in the foregoing methods, an organic solvent or carrier preferably is employed; useful organic solvents include those mentioned previously. In other embodiments, one or more monomers can be used as a carrier or the catalyst ingredients can be employed neat, i.e., free of any solvent of other carrier.

In one or more embodiments, some or all of the catalyst composition can be supported on an inert carrier. The support can be a porous solid such as talc, a sheet silicate, an inorganic oxide or a finely divided polymer powder. Suitable inorganic oxides are oxides of elements from any of Groups 2-5 and 13-16. Exemplary supports include $SiO_2$, aluminum oxide, and also mixed oxides of the elements Ca, Al, Si, Mg or Ti and also corresponding oxide mixtures, Mg halides, styrene/divinylbenzene copolymers, polyethylene or polypropylene.

The production of polymers such as cis-1,4-polydiene (or interpolymers that include cis-1,4-diene mer) is accomplished by polymerizing conjugated diene monomer(s) in the presence of a catalytically effective amount of a catalyst composition as described above. The total catalyst concentration to be employed in the polymerization mass depends on the interplay of multiple factors such as the purity of ingredients, the polymerization temperature, the polymerization rate and conversion desired, and the molecular weight desired. Accordingly, a specific total catalyst concentration cannot be definitively set forth except to say that catalytically effective amounts of the respective catalyst ingredients should be used. The amount of the formula (I) complex used generally ranges from ~0.005 to ~2 mmol, commonly from ~0.01 to ~1 mmol, typically from ~0.02 to ~0.5 mmol per 100 g monomer. All other ingredients generally can be added in amounts based on the amount of formula (I) complex; see the various ratios set forth above.

Where an olefin interpolymer is desired, the molar ratio of polyene (e.g., conjugated diene) to olefin introduced into the reaction vessel can vary over a wide range. For example, the molar ratio of polyene (e.g., conjugated diene) to olefin can range from ~100:1 to 1:100, commonly from ~20:1 to 1:20, and typically from ~5:1 to 1:5.

Polymerization preferably is carried out in one or more organic solvents of the type(s) set forth above, i.e., as a solution polymerization (where both the monomer(s) and the polymers formed are soluble in the solvent) or precipitation polymerization (where the monomer is in a condensed phase but the polymer products are insoluble). The catalyst ingredients preferably are solubilized or suspended in the organic liquid, and additional solvent (beyond that used in preparing the catalyst composition) usually is added to the polymerization system; the additional solvent(s) may be the same as or different from the solvent(s) used in preparing the catalyst composition. In one or more embodiments, the solvent content of the polymerization mixture may be more than 20%, more than 50%, or even more than 80% (by wt.) of the total weight of the polymerization mixture. The concentration of monomer present at the beginning of the polymerization generally ranges from ~3 to ~80%, commonly from ~5 to ~50%, and typically from ~10% to ~30% (by wt.).

In certain embodiments, a bulk polymerization system that includes no more than a minimal amount of solvent can be used, i.e., a bulk polymerization process where one or more of the monomers act(s) as the solvent; examples of potentially useful bulk polymerization processes are disclosed in U.S. Pat. No. 7,351,776. In a bulk polymerization, the solvent content of the polymerization mixture may be less than 20%, less than 10%, or even less than 5% (by wt.) of the total weight of the polymerization mixture. The polymerization mixture even can be substantially devoid of solvent, i.e., contain less than that amount of solvent which otherwise would have an appreciable impact on the polymerization process.

The polymerization can be conducted in any of a variety of reaction vessels. For example, solution polymerizations can be conducted in a conventional stirred-tank reactor. Bulk polymerizations also can be conducted in a stirred-tank reaction if the monomer conversion is less than ~60%. Where monomer conversion is higher than ~60%, which typically results in a highly viscous polymer cement (i.e., mixture of solvent, polymers and any remaining monomer(s)), bulk polymerization can be conducted in an elongated reactor in which the viscous cement is driven by, for example, piston or self-cleaning single- or double-screw agitator.

All components used in or during the polymerization can be combined in a single vessel (e.g., a stirred-tank reactor), and the entirety of the polymerization process can be conducted in that vessel. Alternatively, two or more of the ingredients can be combined outside the polymerization vessel and transferred to another vessel where polymerization of the monomer(s), or at least a major portion thereof, can be conducted.

The polymerization can be carried out as a batch, continuous, or semi-continuous process. The conditions under which the polymerization proceeds can be controlled to maintain the temperature of the polymerization mixture in a range of from −10° to 200° C., commonly from ~0° to ~150° C., and typically from ~20° to ~100° C. Heat generated by the polymerization can be removed by external cooling by a thermally controlled reactor jacket and/or internal cooling (by evaporation and condensation of the monomer through use of a reflux condenser connected to the reactor). Also, conditions may be controlled to conduct the polymerization under a pressure of from ~0.01 to ~5 MPa, commonly from ~0.05 to ~3 MPa, typically from ~0.1 to ~2 MPa; the pressure at which the polymerization is carried out can be such that the majority of monomers are in the liquid phase. In these or other embodiments, the polymerization mixture may be maintained under anaerobic conditions, typically provided by an inert protective gas such as $N_2$, Ar or He.

Regardless of whether a batch, continuous, or semi-continuous process is employed, the polymerization preferably is conducted with moderate to vigorous agitation.

The described polymerization process advantageously results in polymer chains that possess reactive (pseudo-living) terminals, which can be further reacted with one or more functionalizing agents so as to provide a polymer with a terminal functionality. These types of polymers can be referred to as functionalized and are distinct from a propagating chain that has not been similarly reacted. In one or more embodiments, reaction between the functionalizing agent and the reactive polymer can proceed via an addition or substitution reaction.

The terminal functionality can be reactive or interactive with other polymer chains (propagating and/or non-propagating) or with other materials in a rubber compound such as particulate reinforcing fillers (e.g., carbon black). As described above, enhanced interactivity between a polymer and particulate fillers in rubber compounds improves the mechanical and dynamic properties of resulting vulcanizates. For example, certain functionalizing agents can impart a terminal functionality that includes a heteroatom to the polymer chain; such a functionalized polymer can be used in rubber compounds from which vulcanizates can be provided, and that vulcanizates can possess high temperature (e.g., 50° C.) hysteresis losses (as indicated by a reduction in high temperature tan δ values) that are less than those possessed by vulcanizates prepared from similar rubber compounds that do not include such functionalized polymers. Reductions in high temperature hysteresis loss can be at least 5%, at least 10%, or even at least 15%.

The functionalizing agent(s) can be introduced after a desired monomer conversion is achieved but prior to introduction of a quenching agent (a compound with a protic H atom) or after the polymerization mixture has been partially quenched. The functionalizing agent can be added to the polymerization mixture after a monomer conversion of at least 5%, at least 10%, at least 20%, at least 50%, or at least 80%. In certain embodiments, the functionalizing agent is added after complete, or substantially complete, monomer conversion. In particular embodiments, a functionalizing agent may be introduced to the polymerization mixture immediately prior to, together with, or after the introduction of a Lewis base as disclosed in U.S. Pat. No. 8,324,329.

Useful functionalizing agents include compounds that, upon reaction, provide a functional group at the end of a polymer chain without joining two or more polymer chains together, as well as compounds that can couple or join two or more polymer chains together via a functional linkage to form a single macromolecule. The ordinarily skilled artisan is familiar with numerous examples of terminal functionalities that can be provided through this type of post-polymerization functionalization with terminating reagents, coupling agents and/or linking agents. For additional details, the interested reader is directed to any of U.S. Pat. Nos. 4,015,061, 4,616,069, 4,906,706, 4,935,471, 4,990,573, 5,064,910, 5,153,159, 5,149,457, 5,196,138, 5,329,005, 5,496,940, 5,502,131, 5,567,815, 5,610,227, 5,663,398, 5,567,784, 5,786,441, 5,844,050, 6,812,295, 6,838,526, 6,992,147, 7,153,919, 7,294,680, 7,642,322, 7,671,136, 7,671,138, 7,732,534, 7,750,087, 7,816,483, 7,879,952, 8,063,153, 8,088,868, 8,183,324, 8,642,706, etc., as well as references cited in these patents and later publications citing these patents. Specific exemplary functionalizing compounds include metal halides (e.g., $SnCl_4$), $R^{10}_3SnCl$, $R^{10}_2SnCl_2$, $R^{10}SnCl_3$, metalloid halides (e.g., $SiCl_4$), carbodiimides, ketones, aldehydes, esters, quinones, N-cyclic amides, N,N'-disubstituted cyclic ureas, cyclic amides, cyclic ureas, Schiff bases, iso(thio)cyanates, metal ester-carboxylate complexes (e.g., dioxyltin bis(octylmaleate), 4,4'-bis(diethylamino) benzophenone, alkyl thiothiazolines, alkoxysilanes (e.g., $Si(OR^{10})_4$, $R^{10}Si(OR^{10})_3$, $R^{10}_2Si(OR^{10})_2$, etc.), cyclic siloxanes, alkoxystannates, and mixtures thereof (In the foregoing, each $R^{10}$ independently is a $C_1$-$C_{20}$ alkyl group, $C_3$-$C_{20}$ cycloalkyl group, $C_6$-$C_{20}$ aryl group, or $C_7$-$C_{20}$ aralkyl group.) Commonly used exemplary functionalizing compounds include $SnCl_4$, tributyl tin chloride, dibutyl tin dichloride, and 1,3-dimethyl-2-imidazolidinone (DMI).

The amount of functionalizing agent added to the polymerization mixture can depend on various factors including the amount of formula (I) complex used, the type of functionalizing agent, the desired level of functionality, etc. In one or more embodiments, the amount of functionalizing agent may be in a range of from 1 to ~200 moles, commonly from ~5 to ~150 moles, and typically from ~10 to ~100 moles per mole of formula (I) complex.

Because reactive polymer chains slowly self-terminate at high temperatures, the functionalizing agent can be added to the polymerization mixture when or soon after a peak polymerization temperature is observed or, at least in some embodiments, within 30±10 minutes thereafter. Reaction of these types of compounds with a terminally active polymer can be performed relatively quickly (a few minutes to a few hours) at moderate temperatures (e.g., 0° to 75° C.).

The functionalizing agent can be introduced to the polymerization mixture at a location (e.g., within a vessel) where the polymerization, or at least a portion thereof, has been conducted or at a location distinct therefrom. For example, the functionalizing agent can be introduced to the polymerization mixture in downstream vessels including downstream reactors or tanks, in-line reactors or mixers, extruders, or devolatilizers.

Although not mandatory, if desired, quenching can be performed to inactivate any residual reactive copolymer chains and the catalyst composition. Quenching can be conducted by stirring the polymer and an active hydrogen-containing compound, such as an alcohol or acid, for up to ~120 minutes at temperatures of from 25° to ~150° C. In some embodiments, the quenching agent can include a polyhydroxy compound as disclosed in U.S. Pat. No. 7,879,958. An antioxidant such as 2,6-di-t-butyl-4-methylphenol (BHT) may be added along with, before, or after the addition of the quenching agent; the amount of antioxidant employed can be from ~0.2 to 1% (by wt.) of the polymer product. The quenching agent and the antioxidant can be added neat or, if necessary, dissolved in a hydrocarbon solvent or liquid monomer prior to being added to the polymerization mixture.

Once polymerization, functionalization (if any) and quenching (if any) are complete, the various constituents of the polymerization mixture can be recovered. Unreacted monomers can be recovered from the polymerization mixture by, for example, distillation or use of a devolatilizer. Recovered monomers can be purified, stored, and/or recycled back to the polymerization process.

The polymer product can be recovered from the polymerization mixture using known techniques. For example, the polymerization mixture can be passed through a heated screw apparatus, such as a desolventizing extruder, in which volatile substances (e.g., low boiling solvents and unreacted monomers) are removed by evaporation at appropriate temperatures (e.g., ~100° to ~170° C.) and under atmospheric or sub-atmospheric pressure. Another option involves steam desolvation followed by drying the resulting polymer crumbs in a hot air tunnel. Yet another option involves recovering the polymer directly by drying the polymerization mixture on a drum dryer. Any of the foregoing can be combined with coagulation with water, alcohol or steam; if coagulation is performed, oven drying may be desirable.

Recovered polymer can be grafted with other monomers and/or blended with other polymers (e.g., polyolefins) and additives to form resin compositions useful for various applications. The polymer, regardless of whether further reacted, is particularly suitable for use in the manufacture of various tire components including, but not limited to, tire treads, sidewalls, subtreads, and bead fillers. It also can be used as a compatibilizer for elastomeric blends and/or used in the manufacture of hoses, belts, shoe soles, window seals, other seals, vibration damping rubber, and other industrial or consumer products.

When the resulting polymer is utilized in a tread stock compound, it can be used alone or blended with any conventionally employed tread stock rubber including natural rubber and/or non-functionalized synthetic rubbers such as, e.g., one or more of homo- and interpolymers that include just polyene-derived mer units (e.g., poly(butadiene), poly (isoprene), and copolymers incorporating butadiene, isoprene, and the like), SBR, butyl rubber, neoprene, EPR, EPDM, acrylonitrile/butadiene rubber (NBR), silicone rubber, fluoroelastomers, ethylene/acrylic rubber, EVA, epichlorohydrin rubbers, chlorinated polyethylene rubbers, chlorosulfonated polyethylene rubbers, hydrogenated nitrile rubber, tetrafluoroethylene/propylene rubber and the like. When a functionalized polymer(s) is blended with conventional rubber(s), the amounts can vary from ~5 to ~99% of the total rubber, with the conventional rubber(s) making up the balance of the total rubber.

Amorphous silica ($SiO_2$) can be utilized as a filler. Silicas are generally classified as wet-process, hydrated silicas because they are produced by a chemical reaction in water, from which they are precipitated as ultrafine, spherical particles. These primary particles strongly associate into aggregates, which in turn combine less strongly into agglomerates. "Highly dispersible silica" is any silica having a very substantial ability to de-agglomerate and to disperse in an elastomeric matrix, which can be observed by thin section microscopy.

Surface area gives a reliable measure of the reinforcing character of different silicas; the Brunauer, Emmet and Teller ("BET") method (described in *J. Am. Chem. Soc.*, vol. 60, p. 309 et seq.) is a recognized method for determining surface area. BET surface area of silicas generally is less than 450 $m^2/g$, and useful ranges of surface include from ~32 to ~400 $m^2/g$, ~100 to ~250 $m^2/g$, and ~150 to ~220 $m^2/g$.

The pH of the silica filler is generally from ~5 to ~7 or slightly over, preferably from ~5.5 to ~6.8.

Some commercially available silicas which may be used include Hi-Sil™ 215, Hi-Sil™ 233, and Hi-Sil™ 190 (PPG Industries, Inc.; Pittsburgh, Pa.). Other suppliers of commercially available silica include Grace Davison (Baltimore, Md.), Degussa Corp. (Parsippany, N.J.), Rhodia Silica Systems (Cranbury, N.J.), and J.M. Huber Corp. (Edison, N.J.).

Silica can be employed in the amount of 1 to 100 phr, commonly in an amount from ~5 to ~80 phr. The useful upper range is limited by the high viscosity that such fillers can impart.

Other useful fillers include all forms of carbon black including, but not limited to, furnace black, channel blacks and lamp blacks. More specifically, examples of the carbon blacks include super abrasion furnace blacks, high abrasion furnace blacks, fast extrusion furnace blacks, fine furnace blacks, intermediate super abrasion furnace blacks, semireinforcing furnace blacks, medium processing channel blacks, hard processing channel blacks, conducting channel blacks, and acetylene blacks; mixtures of two or more of these can be used. Carbon blacks having a surface area (EMSA) of at least 20 $m^2/g$, preferably at least ~35 $m^2/g$, are preferred; surface area values can be determined by ASTM D-1765 using the CTAB technique. The carbon blacks may be in pelletized form or an unpelletized flocculent mass, although unpelletized carbon black can be preferred for use in certain mixers.

The amount of carbon black can be up to ~50 phr, with 5 to 40 phr being typical. When carbon black is used with silica, the amount of silica can be decreased to as low as ~1 phr; as the amount of silica decreases, lesser amounts of the processing aids, plus silane if any, can be employed.

Elastomeric compounds typically are filled to a volume fraction, which is the total volume of filler(s) added divided by the total volume of the elastomeric stock, of ~25%; accordingly, typical (combined) amounts of reinforcing fillers, i.e., silica and carbon black, is ~30 to 100 phr.

When silica is employed as a reinforcing filler, addition of a coupling agent such as a silane is customary so as to ensure good mixing in, and interaction with, the elastomer(s). Generally, the amount of silane that is added ranges between ~4 and 20%, based on the weight of silica filler present in the elastomeric compound.

Coupling agents generally include a functional group capable of bonding physically and/or chemically with a group on the surface of the silica filler (e.g., surface silanol groups) and a functional group capable of bonding with the elastomer, e.g., via a sulfur-containing linkage. Such coupling agents include organosilanes, in particular polysulfurized alkoxysilanes (see, e.g., U.S. Pat. Nos. 3,873,489, 3,978,103, 3,997,581, 4,002,594, 5,580,919, 5,583,245, 5,663,396, 5,684,171, 5,684,172, 5,696,197, etc.) or polyorganosiloxanes. An exemplary coupling agent is bis[3-(triethoxysilyl)propyl]-tetrasulfide.

Addition of a processing aid can be used to reduce the amount of silane employed. See, e.g., U.S. Pat. No. 6,525,118 for a description of fatty acid esters of sugars used as processing aids. Additional fillers useful as processing aids include, but are not limited to, mineral fillers, such as clay (hydrous aluminum silicate), talc (hydrous magnesium silicate), and mica as well as non-mineral fillers such as urea and sodium sulfate. Preferred micas contain principally alumina, silica and potash, although other variants also can be useful. The additional fillers can be utilized in an amount of up to ~40 phr, typically up to 20 phr.

Other conventional rubber additives also can be added. These include, for example, process oils, plasticizers, antidegradants such as antioxidants and antiozonants, curing agents and the like.

All of the ingredients can be mixed using standard equipment such as, e.g., Banbury or Brabender mixers. Typically, mixing occurs in two or more stages. During the first stage (often referred to as the masterbatch stage), mixing typically is begun at temperatures of 120° to 130° C. and increases until a so-called drop temperature, typically 163°±3° C., is reached.

Where a formulation includes silica, a separate re-mill stage often is employed for separate addition of the silane component(s). This stage often is performed at temperatures similar to, although often slightly lower than, those employed in the masterbatch stage, i.e., ramping from ~90° C. to a drop temperature of ~150° C.

Reinforced rubber compounds conventionally are cured with ~0.2 to ~5 phr of one or more known vulcanizing agents such as, for example, sulfur or peroxide-based curing systems. For a general disclosure of suitable vulcanizing agents, the interested reader is directed to an overview such as that provided in Kirk-Othmer, *Encyclopedia of Chem. Tech.*, 3d ed., (Wiley Interscience, New York, 1982), vol. 20, pp. 365-468. Vulcanizing agents, accelerators, etc., are added at a final mixing stage. To ensure that onset of vulcanization does not occur prematurely, this mixing step often is done at lower temperatures, e.g., starting at ~60° to ~65° C. and not going higher than ~105° to ~110° C.

The following non-limiting, illustrative examples provide the reader with detailed conditions and materials that can be useful in the practice of the present invention. In the chemical structures shown in those examples, "Me" represents a methyl group and "t-Bu" represents a tert-butyl group.

EXAMPLES

Example 1a

2-[3,5-bis(trifluoromethyl)phenyl]indene

A 500 mL, three-necked flask was equipped with a magnetic stir bar, reflux condenser, and a dropping funnel that was dried in an oven for at least 12 hours and purged with dried Ar.

To this flask were added 1.01 g (42.1 mmol) Mg turnings and 200 mL dry diethyl ether. Activation of the Mg was accomplished by adding 0.2 mL 1,2-dibromoethane and gently heating, with stirring, until the ether refluxed without further inputted heat. Thereafter, 7.25 mL (42.1 mmol) 1,3-bis(trifluoromethyl)-5-bromobenzene in 50 mL diethyl ether was added with stirring to the dropping funnel and then added to the flask at such a rate that a gentle reflux was maintained, i.e., about 2 hours.

After the foregoing addition, the flask was placed into an oil bath and heated to reflux for ~12 hours, after which the mixture was cooled and filtered (to remove any remaining magnesium) into a separate dried, purged three-necked, 500 mL flask arranged identically to the one used previously.

To the funnel was added 5.00 g (37.9 mmol) 2-indanone in 50 mL dry diethyl ether, which then was added dropwise to the freshly prepared Grignard reagent with stirring at room temperature over the course of ~1 hour. After addition, the resulting mixture was further stirred at room temperature for ~12 hours before the mixture was cooled to 0° C. and quenched with 100 mL of a saturated solution of NH$_4$Cl.

The mixture was extracted with two 150 mL-portions of ethyl acetate. The organic layers were collected and dried over Na$_2$SO$_4$ and concentrated on a rotary evaporator. The crude mixture was placed under a high vacuum (<1 torr, ~100 Pa) to further remove any volatiles.

The resulting crude mixture was re-dissolved in 150 mL toluene, 0.60 g (3.15 mmol) p-toluenesulfonic acid monohydrate. The flask was then equipped with a Dean-Stark apparatus and condenser and then stirred and heated to reflux. Progress of the reaction was monitored by the collection of water, with confirmation by TLC.

After consumption of the starting material, the reaction mixture was allowed to cool to room temperature before 100 mL saturated NaHCO$_3$ was added. The organic layer was extracted with two 50 mL-portions of diethyl ether.

All of the organic layers were collected and dried over Na$_2$SO$_4$ and concentrated on a rotary evaporator. The crude mixture was placed under a high vacuum (<1 torr, ~100 Pa) to further remove any volatiles.

Column chromatography (100% hexanes) was used to isolate 5.4 g (43.5% yield based on 2-indanone) of an off-white solid, 2-[3,5-bis(trifluoromethylphenyl)]indene:

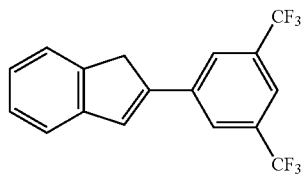
(IIIa)

Example 1b

3-[3,5-bis(trifluoromethyl)phenyl]indene

The process of Example 1a was repeated, with the exception that 5.00 g (37.9 mmol) 1-indanone in 50 mL dry diethyl ether was added dropwise to the Grignard reagent.

The product recovered was 7.3 g (58.9% yield based on 1-indanone) of a yellow tinted oil, 3-[3,5-bis(trifluoromethylphenyl)]indene:

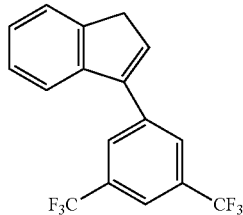
(IIIb)

Example 1c 3-(2,3,4,5,6-pentafluorophenyl)indene

The process of Example 1b was repeated, with the exception that 5.24 mL (42.1 mmol) 1-bromo-2,3,4,5,6-pentafluorobenzene was used in place of 1,3-bis(trifluoromethyl)-5-bromobenzene.

The product recovered was 2.0 g (18.7% yield based on 1-indanone) of a white crystalline solid, 3-(2,3,4,5,6-pentafluorophenyl)indene:

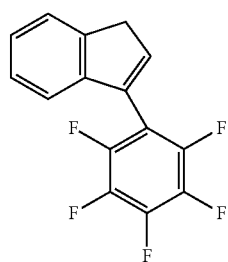
(IIIc)

Example 2a

2-[3,5-bis(tert-butyl)phenyl]indene

The process of Example 1a was repeated with the following exceptions: (1) 11.3 g (42.1 mmol) 1-bromo-3,5-di-tert-butylbenzene was used in place of 1,3-bis(trifluoromethyl)-5-bromobenzene, and (2) after concentration on a rotary evaporator but before being placed under high vacuum, the reaction mixture was passed (with 100% hexanes) through a pad of silica gel to remove non-polar material, with ethyl acetate used to collect the tertiary alcohol product.

The product recovered was 1.4 g (12.1% yield based on 2-indanone) of a white waxy solid, 2-[3,5-bis(tert-butyl)phenyl]indene:

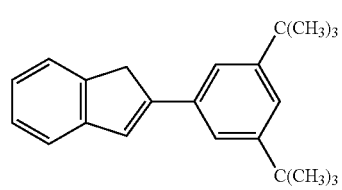
(IVa)

Example 2b

3-[3,5-bis(tert-butyl)phenyl]indene

The process of Example 2a was repeated, with the exception that 5.00 g (37.9 mmol) 1-indanone in 50 mL dry diethyl ether was added dropwise to the Grignard reagent.

The product recovered was 10.1 g (87.0% yield based on 1-indanone) of a viscous, yellowish oil, 3-[3,5-bis(tert-butyl)phenyl]indene:

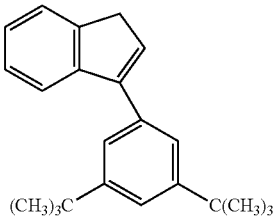

(IVb)

Example 2c

3-[4-(tert-butyl)phenyl]indene

The process of Example 2b was repeated, with the exception that 7.3 mL (42.1 mmol) 1-bromo-4-tert-butylbenzene was used in place of 1-bromo-3,5-di-tert-butylbenzene.

The product recovered was 2.8 g (29.8% yield based on 1-indanone) of an off-white waxy solid, 3-[4-(tert-butyl)phenyl]indene:

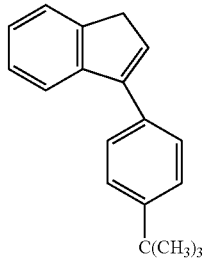

(IVc)

Example 2d

2-[4-(tert-butyl)phenyl]indene

The process of Example 2c was repeated, with the exception that 5.00 g (37.9 mmol) 2-indanone in 50 mL dry diethyl ether was added dropwise to the Grignard reagent.

The product recovered was 3.5 g (37.2% yield based on 2-indanone) of a yellowish oil, 2-[4-(tert-butyl)phenyl]indene:

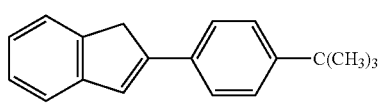

(IVd)

In summary, Examples 1a-1c and 2a-2d relate to indene compounds that include phenyl substituents. Examples 1a-1c include electron withdrawing atoms or groups on the phenyl substituents, while Examples 2a-2d include electron donating groups on the phenyl substituents.

Each of these compounds was used in the preparation of general formula (I)-type Group 3 metal complexes. To permit better inter-complex comparisons in terms of, for example, synthetic yields and catalytic activity, each of these general formula (I)-type complexes involved M=Gd, z=0, n=2 and $R^2$=—N[SiH(CH$_3$)$_2$]$_2$. This similarity is not to be deemed limiting but, instead, as permitting better comparison of the effects of different indenyl ligands.

Example 3a

Complex with 2-[3,5-bis(trifluoromethyl)phenyl] indenyl ligands

Under Ar, 2.78 mL (15.7 mmol) 1,1,3,3-tetramethyldisilazane was slowly added to a brownish mixture of 2.50 g (3.9 mmol) Gd{N[Si(CH$_3$)$_3$]$_2$}$_3$ (hereinafter "Gd[N(TMS)$_2$]$_3$") and 2.52 g (7.7 mmol) of the formula (IIIa) compound from Example 1a in 30 mL hexane. This mixture was stirred at 70° C. overnight (>12 hours), during which time a yellow solution with some greenish precipitate formed.

The reaction vessel was cooled to room temperature before the solution was transferred to a flask under Ar. All volatiles were removed under vacuum, and the product was re-dissolved in 30 mL hexane.

That solution was transferred to a freezer set at –30° C. The resulting yellow solution was decanted.

The product recovered, after drying under vacuum, was 2.5 g (~69% yield) of a bright yellow solid having the following structure:

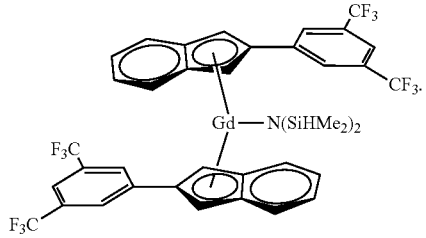

(Va)

Example 3b

Complex with 3-[3,5-bis(trifluoromethyl)phenyl] indenyl ligands

The process of Example 3a was repeated, with the exception that 2.52 g (7.7 mmol) of the formula (IIIb) compound from Example 1b was used in place of the formula (IIIa) compound in the initial brownish mixture. The overnight reaction mixture was a green solution with a small but noticeable amount of precipitate.

The reaction vessel was cooled to room temperature before the solution was transferred to a flask under Ar. All volatiles were removed under vacuum.

The product recovered, after drying under vacuum, was 3.3 g (~91% yield) of a greenish solid having the following structure:

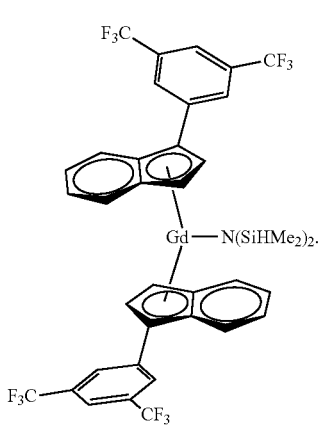

(Vb)

Example 3c

Complex with 3-(2,3,4,5,6-pentafluorophenyl)indenyl ligands

The process of Example 3b was repeated, with the exceptions that the amount of Gd[N(TMS)$_2$]$_3$ was reduced to 1.38 g (2.16 mmol) and that 1.20 g (4.25 mmol) of the formula (IIIc) compound from Example 1c was used in place of the formula (IIIb) compound, which provided an initial clear yellow solution. The overnight reaction mixture was a yellowish solution with a small but noticeable amount of precipitate.

The reaction vessel was cooled to room temperature before the solution was transferred to a flask under Ar. All volatiles were removed under vacuum.

The product recovered, after solvent removal under vacuum, was 1.8 g (~97% yield) of a viscous yellowish red oil having the following structure:

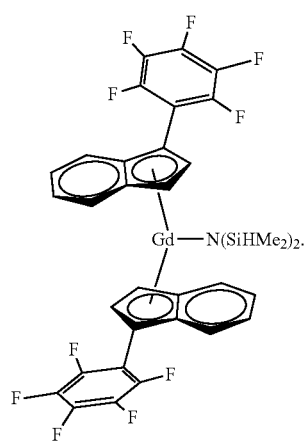

(Vc)

Example 4a

Complex with 2-[3,5-bis(tert-butyl)phenyl]indenyl ligands

Under Ar, 1.68 mL (9.50 mmol) 1,1,3,3-tetramethyldisilazane was slowly added to a mixture of 1.51 g (2.40 mmol) Gd[N(TMS)$_2$]$_3$ and 1.41 g (4.60 mmol) of the formula (IVa) compound from Example 2a in 30 mL hexane. This mixture was stirred at 80° C. overnight (>12 hours), during which time a yellow solution formed.

The reaction vessel was cooled to room temperature before the solution was transferred to a flask under Ar. All volatiles were removed under vacuum, and the yellow oily residue was re-dissolved in 5 mL hexane.

That solution was transferred to a freezer set at −30° C., but no precipitate formed. Solvent then was removed under vacuum.

The product recovered was 2.04 g (~98% yield) of a waxy yellow solid having the following structure (with "t-Bu" representing a —C(CH$_3$)$_3$ group):

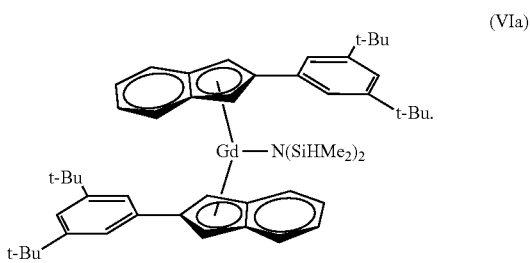

(VIa)

Example 4b

Complex with 3-[3,5-bis(tert-butyl)phenyl]indenyl ligands

Under Ar, 2.22 mL (12.5 mmol) 1,1,3,3-tetramethyldisilazane was slowly added to a mixture of 2.00 g (3.10 mmol) Gd[N(TMS)$_2$]$_3$ and 1.87 g (6.10 mmol) of the formula (IVb) compound from Example 2b in 30 mL hexane. This mixture was stirred at 80° C. overnight (>12 hours), during which time a red solution formed.

The reaction vessel was cooled to room temperature before the volatiles were removed under vacuum. The red oily residue was re-dissolved in 10 mL hexane.

That solution was transferred to a freezer set at −30° C., but no precipitate formed. Solvent then was removed under vacuum.

The product recovered was 2.76 g (~100% yield) of a red viscous oil having the following structure:

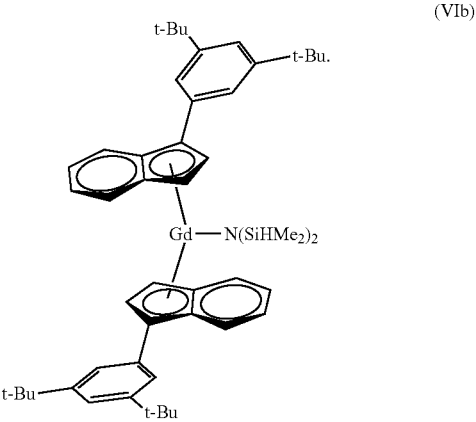

(VIb)

Example 4c

Complex with 3-[4-(tert-butyl)phenyl]indenyl ligands

The process of Example 4b was repeated, with the exception that 1.52 g (6.10 mmol) of the formula (IVc) compound from Example 2c was used in place of the formula (IVb) compound in the initial mixture. This mixture was stirred at 70° C. overnight (>12 hours), during which time a yellow solution with some precipitate formed.

The reaction vessel was cooled to room temperature before the solution was transferred to a flask under Ar. All volatiles were removed under vacuum, and the product was re-dissolved in 6 mL hexane.

That solution was transferred to a freezer set at −30° C. The liquid portion then was removed.

The product recovered, after drying under vacuum, was 2.1 g (~87% yield) of an orange solid having the following structure:

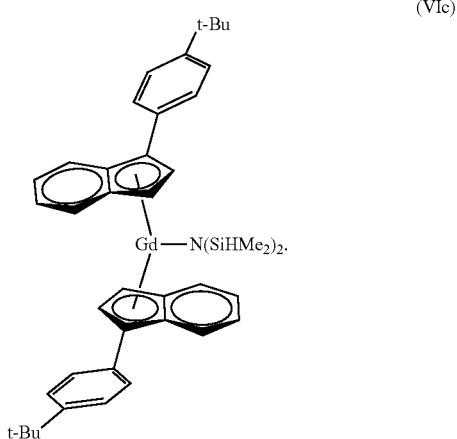

(VIc)

Example 4d

Complex with 2-[4-(tert-butyl)phenyl]indenyl ligands

The process of Example 4c was repeated, with the exception that the formula (IVd) compound from Example 2d was used in place of the formula (IVc) compound in the initial mixture.

The product recovered, after drying under vacuum, was 1.91 g (~79% yield) of a bright yellow crystalline solid having the following structure:

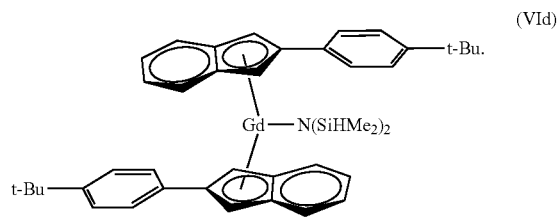

(VId)

Examples 5-11

Copolymerizations

Each of the complexes from Examples 3a-3c and 4a-4d was used to polymerize butadiene and ethylene. (To assist in comparing the effects of the complexes as catalyst components, as many other potential variables as possible were held constant; however, this should not be considered to be limiting. Monoethylenically unsaturated monomers (e.g., α-olefins) other than ethylene and polyenes other than butadiene certainly can be used instead of or in addition to those used here. Additionally, other parameters of the polymerization certainly can be changed.)

The following procedure was used in each of the polymerizations.

To a dry, $N_2$-purged stainless steel 5 L vessel was added 1.80 kg dry toluene and 0.20 kg purified, dry butadiene before the reactor was pressurized to 0.2 MPa with ethylene. The reactor agitator was initiated, the jacket was heated to 50° C., and the reactor contents were allowed to equilibrate to that temperature.

During equilibration, in an argon glovebox, 50 mL dry toluene followed by 3.53 mL of a 1.02 M solution of diisobutyl aluminum hydride, the gadolinium catalyst (see Table 1 below), and finally 38.0 mg (47.3 mmol) solid N,N-dimethylanilinium tetra(pentafluorophenyl)borate was added to a 200 mL bottle that was previously dried and $N_2$-purged. The mixture was sealed and removed from the glovebox.

The contents of the small bottle were injected into the reactor, and gaseous dried ethylene was allowed to fill the reactor to a final pressure of 1.72 MPa. The jacket temperature of the reactor was increased to ~80° C.

After ~120 minutes, each polymer cement was dropped into a vat of 2-propanol containing 2,6-di-tert-butyl-4-methylphenol.

Recovered polymer was drum-dried at 120° C.

The amounts of polymer, mer content and other properties also are summarized below in Table 1. Mole percentages were calculated from $^1H$ NMR spectroscopic data, while molecular weight information was determined by GPC.

TABLE 1

| Catalyst information and polymer properties | | | | | | | |
|---|---|---|---|---|---|---|---|
| | 5 | 6 | 7 | 8 | 9 | 10 | 11 |
| complex, Example # | 3a | 3b | 3c | 4a | 4b | 4c | 4d |
| Amt. of complex, mg | 42.6 | 42.6 | 38.4 | 40.4 | 40.4 | 35.4 | 35.4 |
| Amt. of complex, μmol | 47.3 | 47.3 | 45.0 | 45.0 | 45.0 | 45.0 | 45.0 |
| Amt. of polymer, g | 212.0 | 198.0 | 233.0 | 236.3 | 246.7 | 239.0 | 213.0 |
| ethylene mer, mol % | 19.7 | 13.8 | 18.3 | 33.2 | 36.3 | 29.0 | 14.0 |
| butadiene mer, mol % | 80.3 | 86.2 | 81.7 | 66.8 | 63.7 | 71.0 | 86.0 |
| 1,4 BD mer, % | 98.3 | 98.6 | 98.6 | 98.9 | 99.0 | 98.8 | 98.5 |
| 1,2-vinyl BD mer, % | 1.7 | 1.4 | 1.4 | 1.1 | 1.0 | 1.2 | 1.5 |

TABLE 1-continued

| Catalyst information and polymer properties | | | | | | | |
|---|---|---|---|---|---|---|---|
| | 5 | 6 | 7 | 8 | 9 | 10 | 11 |
| $M_n$ (kg/mol) | 96.6 | 115.8 | 45.0 | 45.8 | 41.5 | 54.1 | 73.6 |
| $M_w/M_n$ | 5.07 | 6.57 | 11.3 | 11.5 | 14.3 | 9.95 | 7.36 |
| $T_g$ (° C.) | −105.0 | −105.1 | — | −104.5 | −105.0 | −105.1 | −105.4 |
| 1st $T_m$ (° C.) | −12.7 | −11.3 | — | −10.2 | −10.3 | −10.5 | −10.6 |
| 2nd $T_m$ (° C.) | 107.3 | 103.2 | — | 118.0 | 115.3 | 113.5 | 113.5 |

All of the complexes were capable of being utilized in coordination catalyst systems, and all provided ethylene/butadiene copolymers having low amounts of vinyl configuration.

The complexes having aryl (phenyl) substituents with R' groups generally resulted in lower ethylene (olefin) contents than those with R" groups.

That which is claimed is:

1. A process for providing a polymer, said process comprising
a) contacting ethylenically unsaturated hydrocarbons that comprise at least one polyene and at least one α-olefin with a catalyst composition that comprises a catalyst activator and a complex defined by the general formula

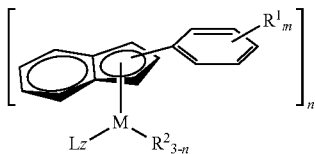

where
M represents a Group 3 metal atom;
L represents a neutral Lewis base;
z is an integer of from 0 to 3 inclusive;
m is an integer of from 1 to 5 inclusive;
n is 1 or 2;
each $R^1$ is an electron withdrawing group or atom or an electron donating group or atom; and
$R^2$ is an X-type, monoanionic ligand,
with the proviso that the $R^1$-containing phenyl group is attached at either the 2- or 3-positions of the indenyl ligand, and
b) allowing said polymer to form from said ethylenically unsaturated hydrocarbons.

2. The process of claim 1 wherein said at least one polyene comprises a conjugated diene.

3. The process of claim 1 wherein said at least one α-olefin comprises ethylene.

4. The process of claim 1 wherein said at least one α-olefin is ethylene.

5. The process of claim 4 wherein said polymer comprises from more than zero up to 40% mole percent ethylene mer.

6. The process of claim 5 wherein said polymer comprises less than 2% polyene mer incorporated in a vinyl configuration.

7. The process of claim 1 wherein z in said general formula is 0.

8. The process of claim 1 wherein M in said general formula is a lanthanide metal atom.

9. The process of claim 1 wherein n in said general formula is 2.

10. The process of claim 1 wherein each $R^1$ in said general formula is a haloalkyl group.

11. The process of claim 2 wherein each haloalkyl group is a trifluoromethyl group.

12. The process of claim 11 wherein m in said general formula is 2.

13. The process of claim 10 wherein m in said general formula is 2.

14. The process of claim 1 wherein each $R^1$ in said general formula is an electron donating group independently selected from $C_1$-$C_6$ alkyl groups.

15. The process of claim 14 wherein each $R^1$ in said general formula is a tert-butyl group.

16. The process of claim 15 wherein m in said general formula is 1.

17. The process of claim 14 wherein m in said general formula is 1.

18. The process of claim 1 wherein said catalyst activator comprises an alkylating agent.

19. The process of claim 1 wherein said catalyst activator comprises a non-coordinating anion or a non-coordinating anion precursor.

20. A process for providing a polymer, said process comprising
a) contacting ethylenically unsaturated hydrocarbons that comprise at least one conjugated diene and ethylene with a catalyst composition that comprises a catalyst activator and a complex defined by the general formula

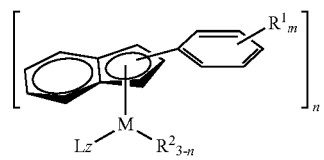

where
M represents a Group 3 metal atom;
L represents a neutral Lewis base;
z is an integer of from 0 to 3 inclusive;
n is 1 or 2;
each $R^1$ is an electron withdrawing group or atom or an electron donating group or atom, with the proviso that m is 2 when each $R^1$ is an electron withdrawing group or m is 1 when $R^1$ is an electron donating group; and
$R^2$ is an X-type, monoanionic ligand,
with the proviso that the $R^1$-containing phenyl group is attached at either the 2- or 3-positions of the indenyl ligand, and
b) allowing said polymer to form from said ethylenically unsaturated hydrocarbons.

* * * * *